United States Patent [19]

Brattsand et al.

[11] Patent Number: 6,140,308
[45] Date of Patent: Oct. 31, 2000

[54] COLON OR ILEUM-SPECIFIC GLUCOCORTICOSTEROID DERIVATIVES

[75] Inventors: Ralph Lennart Brattsand, Lund; Peter Edman, Bjärred; Thomas Högberg, Åkarp; Stinabritt Nilsson, Lund; Bror Arne Thalen, Bjärred; Jan Erik Ulmius, Lund, all of Sweden

[73] Assignee: Aktiebolaget Astra, Sweden

[21] Appl. No.: 09/261,247

[22] Filed: Mar. 3, 1999

Related U.S. Application Data

[62] Division of application No. 08/764,985, Dec. 13, 1996, Pat. No. 5,908,833, which is a continuation of application No. 08/451,887, May 26, 1995, abandoned, which is a continuation of application No. 08/178,773, Jan. 7, 1994, abandoned.

[30] Foreign Application Priority Data

| Jan. 8, 1993 | [SE] | Sweden | 9300030 |
| Jan. 14, 1993 | [SE] | Sweden | 9300082 |

[51] Int. Cl.$^7$ .................................................. A61K 31/70
[52] U.S. Cl. ........................................... 514/26; 514/178
[58] Field of Search .......................... 514/26, 178; 536/5

[56] References Cited

U.S. PATENT DOCUMENTS

| 3,928,326 | 12/1975 | Brattsand et al. | 260/239.55 |
| 3,929,768 | 12/1975 | Brattsand et al. | 540/63 |
| 3,983,233 | 9/1976 | Brattsand et al. | 424/241 |
| 3,992,534 | 11/1976 | Brattsand et al. | 424/241 |
| 3,996,359 | 12/1976 | Brattsand et al. | 424/241 |
| 4,207,316 | 6/1980 | Schöttle et al. | 424/243 |
| 4,221,787 | 9/1980 | Bodor et al. | 424/241 |
| 4,224,320 | 9/1980 | Dahl et al. | 424/243 |
| 4,404,200 | 9/1983 | Thalen et al. | 424/241 |
| 4,443,440 | 4/1984 | Anderson et al. | 424/243 |
| 4,456,602 | 6/1984 | Anderson et al. | 424/243 |
| 4,469,689 | 9/1984 | Anderson et al. | 424/243 |
| 4,472,392 | 9/1984 | Anderson et al. | 424/243 |
| 4,548,922 | 10/1985 | Carey et al. | 514/4 |
| 4,588,718 | 5/1986 | Anderson et al. | 514/172 |
| 4,693,999 | 9/1987 | Axelsson et al. | 514/174 |
| 4,820,700 | 4/1989 | Brattsand et al. | 514/174 |
| 4,882,315 | 11/1989 | Chiodini et al. | 514/26 |
| 4,895,836 | 1/1990 | Chiodini et al. | 514/26 |
| 4,920,099 | 4/1990 | Chiodini et al. | 514/26 |
| 4,959,358 | 9/1990 | Carey et al. | 514/171 |
| 5,023,239 | 6/1991 | Ogura et al. | 514/26 |
| 5,126,330 | 6/1992 | Ogura et al. | 514/26 |
| 5,215,979 | 6/1993 | Andersson et al. | 514/172 |
| 5,643,602 | 7/1997 | Ulmius | 424/462 |
| 5,888,995 | 3/1999 | Axelsson et al. | 514/174 |
| 5,908,833 | 6/1999 | Brattsand et al. | 514/26 |
| 5,939,409 | 8/1999 | Andersson et al. | 514/174 |

FOREIGN PATENT DOCUMENTS

| 0123485 | 4/1984 | European Pat. Off. . |
| PCT/SE90/ 00738 | 5/1991 | WIPO . |
| WO 91/07172 | 5/1991 | WIPO . |
| WO 92/13873 | 8/1992 | WIPO . |
| WO 93/22334 | 11/1993 | WIPO . |

OTHER PUBLICATIONS

Haeberlin et al. "In Vitro Evaluation of Dexamethansone–beta–D–Glucuronide for Colon–Specific Drug Delivery", Pharmaceutical Research, vol. 10, No. 11, pp. 1553–1562, 1993.
Friend et al. "Colon–specific drug delivery from a glucoside prodrug in the guinea–pig, efficacy study", Journal of Controlled Release, vol. 15, pp. 47–54, 1991.
Mattox et al. "Synthesis of C–21 Glucosiduronates of Cortisone and Related Corticosteroids", Biochemistry, vol. 8, No. 3, pp. 1188–1199, Mar. 1969.
Nitta et al. Studies on Steroids. III. The Preparation of Steroid–21–yl–glucopyranosiduronamides, Chem. Pharm. Bull., vol. 12, No. 4, pp. 450–453, 1964.
Friend, David R. "Colon Specific Drug Delivery", Advanced Drug Delivery News, vol. 7, pp. 149–199, 1991.
Brattsand, "Overview of Newer Glucocorticosteroid Preparations for Inflammatory Bowel Disease", Can. J. Gastroenterol., 4:407–414, 1990.
Conchie et al., "Mammalian Glycosidases Distribution in the Body", The Biochem. J., 71:318–325, 1959.
Empey et al., Synthesis of a Novel Clucocorticoid–conjugate which Accelerates Colitis Healing without Adrenal Suppression, Gastroenterology, 104:A1038, 1993.
Empey et al., "Colon–Specific Corticosteroid Drug delivery Accelerates Healing without Adrenal Suppression During Experiment Colitis", Clin. Invest. Med., 15:A46, 1992.
Friend, "Colon–specific Drug Delivery", Advanced Drug Delivery Reviews, 7:149–199, 1991.
Friend et al., "A Colon–Specific Drug–Delivery System Based on Drug Glycosides and the Glycosidases of Colonic Bacteria", J. Med. Chem., 27:261–266, 1984.
Friend et al., "Drug glycosides: Potential Produrgs for Colon–Specific Drug Delivery", J. Med. Chem., 27: 51–57, 1985.
Greenberg et al., "Oral Budesonide for Active Crohn's Disease", N. Engl. J. Med., 331:836–841, 1994.
Hawkesworth et al., "Intestinal Bacteria and the Hydrolysis of Glycosidic Bonds", J. Med. Microbiol., 4:451–459, 1971.
Hsu et al., "Lysosomal enzymes of Rat Intestinal Mucosa", J. Cell Biol., 23:233–240, 1964.
McLeod et al., "A Glucocorticoid Prodrug Facilitates Normal Mucosal Function in Rat Colitis without Adrenal Suppression", gastroenterology, 106:405–413, 1994.
Peters et al., "Enzyme Activities and Properties of Lysosomes and Brush Borders in Jejunal Biopsies from Control Subjects and Patients with Coeliac Disease", Clinical Sci. & Mol. Med., 48:259–267, 1975.
Tozer et al., "Colon–Specific Delivery of Dexamethasone from a Glucoside Prodrug in the Guinea Pig", Pharmaceutical Res., 8:445–454, 1991.

*Primary Examiner*—Howard C. Lee
*Attorney, Agent, or Firm*—Fish & Richardson P.C.

[57] ABSTRACT

Novel compounds which are a glucocorticosteroid (GCS) chemically bound to a sugar, having the general formula

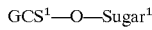

$GCS^1$—O—$Sugar^1$ for colon- or ileum-specific delivery of the GCS to inflamed bowel mucosa, as well as processes for their preparation, pharmaceutical preparations containing the compounds and the use of said compounds in therapy.

43 Claims, No Drawings

COLON OR ILEUM-SPECIFIC GLUCOCORTICOSTEROID DERIVATIVES

This application is a divisional of U.S. application Ser. No. 08/764,985, filed Dec. 13, 1996 now U.S. Pat. No. 5,908,833 which is a continuation of U.S. application Ser. No. 08/451,887, filed May 26, 1995, now abandoned, which is a continuation of U.S. application Ser. No. 08/178,773, filed Jan. 7, 1994, now abandoned.

FIELD OF THE INVENTION

The present invention relates to novel compounds which are a glucocorticosteroid (GCS) chemically bound to a sugar, for local colon- or ileum-specific delivery of the GCS to inflamed bowel mucosa and to processes for their preparation. The invention also relates to pharmaceutical preparations containing the compounds, and to the use of said compounds in therapy. Also pharmaceutically and pharmacologically acceptable salts of the compounds according to the invention are comprised.

The object of the invention is to provide an anti-inflammatory GCS, with a high first pass metabolism in the liver, chemically bound to a sugar, or a pharmaceutical composition of the GCS-sugar compound for local colon- or ileum-specific delivery of the GCS to the inflamed bowel muccosa.

BACKGROUND OF THE INVENTION

Ulcerative colitis (UC) is a serious inflammatory disease affecting the colon and then most often the descendens and sigmoideum segments of colon. Morbus Crohn is a dangerous inflammatory bowel disease, sometimes affecting primarily colon but most often affecting the terminal small bowel—the ileum. These inflammatory processes are sensitive to GCS therapy, but hitherto effective long term treatment has been hampered by serious adverse GCS effects in the systemic circulation (eg osteoporosis, precipitation of diabetes, blocked HPA-axis etc).

In order to locally treat the mainly affected distal part of colon, the luminal concentration of steroid in colon must be high enough to allow for intraluminal transport despite a competing systemic absorption in the colon ascendens. The ideal profile for colon-specific therapy would be reached by release of a potent GCS with a very high first pass metabolic inactivation in the liver. There should be a continous and complete release of the active GCS during the colon passage. The best therapy has hitherto been attained with budesonide, which has a favourable combination of high topical potency and substantial hepatic first pass inactivation, Can J Gastroenterol 4:407–414, 1990. To reach colon mucosa of the distal segments by local therapy, budesonide has to be encapsulated in a pharmaceutical formulation, which when given orally starts to release budesonide in the terminal ileum. Such a pharmaceutical formulation is disclosed in PCT/SE90/00738. However, with a pharmaceutical formulation of that kind it is difficult to get a complete GCS release during the colonic transit, which at least in periods of active disease is short and quite variable. Thus, a substantial fraction of GCS is often bypassing the patient without being released.

An approach to more specific therapy of colon, has been a chemical targeting based on bacteria-specific cleavage of a GCS prodrug, e g a β-D-glucoside. In EP 123485 and also in J Med Chem 28:51–57, 1985, in Pharmacutical Res 8:445–454, 1991, and in Advanced Drug Delivery Reviews 7:149–199, 1991, such prodrugs have recently been described based on dexamethasone and hydrocortisone. However, these GCS-glycosides will not be colon-specific as stated, because the released glucocorticosteroids have too low first pass inactivation in the liver (Can. J. Gastroenterol. 4:407–414, 1990). In man a substantial fraction of the GCS released can be anticipated to reach the systemic circulation intact and by that provoke adverse reactions. Furthermore, plain delivery of GCS-glycoside will not lead to the right type of continous colonic release. When the glycoside meets glycosidase-containing bacteria in cecum and ascending colon, a rapid intraluminal hydrolysis and GCS absorption will occur. This reduces markedly the possibilities for subsequent local release in colon transversum, descendens, sigmoideum and rectum, which parts are all more prone to colitis than what ascendens is. This poor local spreading of active GCS from glycosdide prodrug has not been discussed earlier.

The most common location of lesions in Morbus Crohn is the ileum. Once the ileum is affected, these patients are very often operated by resection of terminal ileum including the ileo-caecal valve, which is the valve normally blocking colonic bacterial backwash into the ileum. There is a recent piece of information that this fecal contamination into bowel segments not normally exposed to high bacterial counts, contributes to the common retrograde spreading of serious inflammation and recurrence of clinical disease. Often these patients have to be operated by further ileal resection or to widening of ileal lumen. Current GCS treatment of Morbus Crohn of small bowel is based on conventional tablets releasing their steroid content in upper bowel segments. Because these tablets work via the systemic route and high doses have to be given, serious adverse effects are provoked. Recently retarded formulations have been tested for improving direct release to ileal mucosa. However, with the current type of retarded formulations controlled by pH and osmotic forces, it is not possible to reach a concentrated release of active GCS at the front of bacterial invasion of small bowel. The use of steroid glycosides in local treatment of ileal Morbus Crohn has not been discussed earlier.

DISCLOSURE OF THE INVENTION

According to the present invention new compounds are disclosed providing a new way to reach a colon-specific delivery better related to the appropriate distribution of mucosal inflammation.

The ideal profile for local treatment of small bowel inflammation in Morbus Crohn (especially in resected patients or in patients with poor function of the ileo-cekal valve) is a GCS-glycoside releasing a potent GCS with very high first pass metabolism in the liver. When a compound of that kind meets the bacterial front at ileal level, it is anticipated that much higher local concentrations of active GCS can be reached at the bacterial front than by earlier types of pharmaceutical formulations.

The compounds according to the invention have the general formula

$$GCS^1\text{—}O\text{—}Sugar^1$$

where $GCS^1$ is a steroid ($GCS^1$—OH) with a high first-pass metabolism in the liver and $Sugar^1$ is recognizable as substrate by bacterial glycosidases and linked to the 21-position of the steroid via a glycosidic bond that is hydrolyzed by glycosidases in the colonic microflora.

GCS[1] can be chosen as a steroid with a 16,17-acetal grouping, providing an additional easily metabolized moiety, which is described by formula I

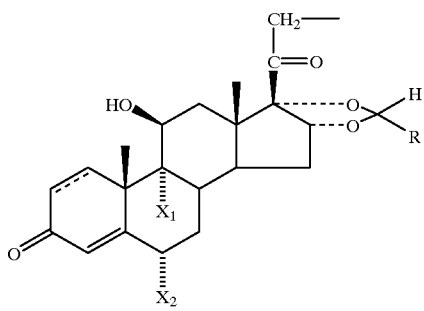

I or the GCS[1] can be a 6-halogenated acetonide described by formula II

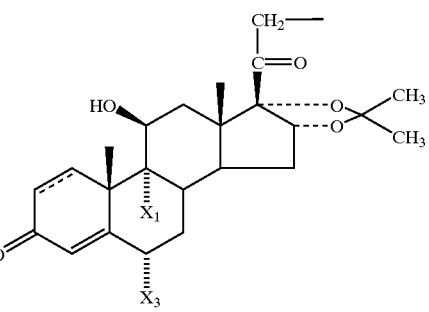

II

R being a hydrocarbon chain with 1 to 9 carbon atoms, the $C_1$–$C_2$ bond being a single or a double bond, $X_1$ and $X_2$ being independently selected for the group consisting of hydrogen, flouro, chloro, and bromo substituents and $X_3$ being a fluoro, chloro or bromo substituent.

The 1,2-position of the GCS[1] a saturated bond or a double bond.

The acetal I is in epimerically pure form i.e. the acetal I is the corresponding pure 22R-epimer, IA, or 22S-epimer, IB

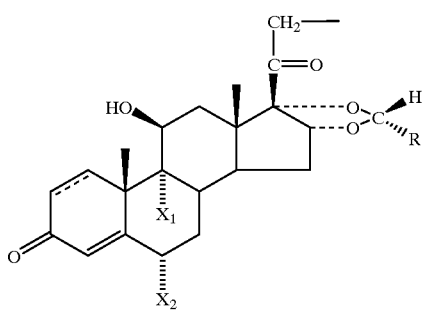

II

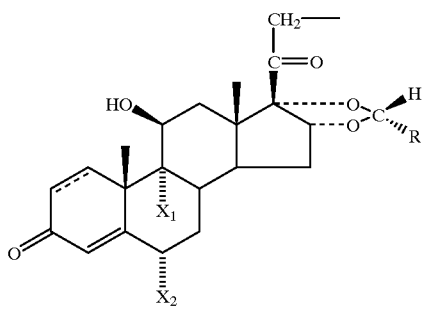

IA

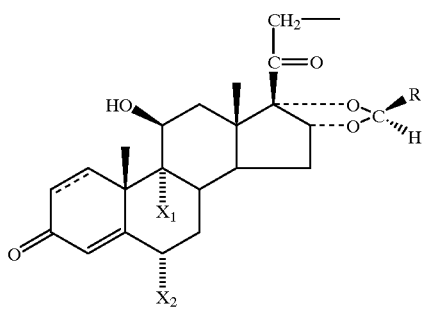

IB or is in the form of an epimeric mixture.

Preferably the acetal I is the 22R-epimer.

Most preferred GCS[1] of the invention is the 22R-epimer of budesonide (GCS[1] —OH) with the formula III

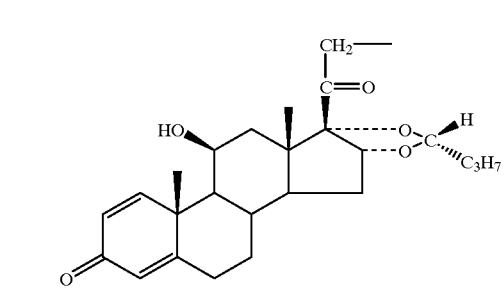

III or the 22R-epimer of 16α,17α-butylidenedioxy-6α,9α-difluoro-11β-hydroxy-4-pregnene-3,20-dione-21-yl, hereinafter called the 22R-epimer of GCS[1] IV, with the formula

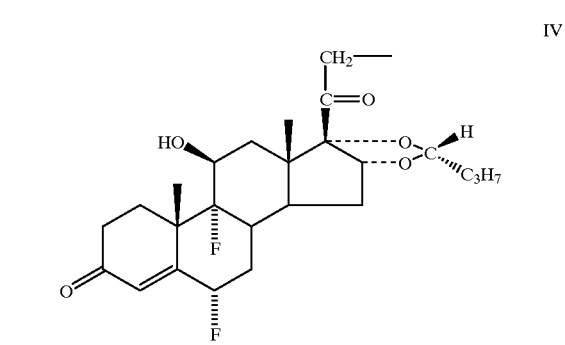

IV or the 22R-epimer of 16α,17α-butylidenedioxy-6α,9α-difluoro-11β-hydroxy-1,4-pregnadiene-3,20-dione-21-yl, hereinafter called the 22R-epimer of GCS[1] V, with the formula

V

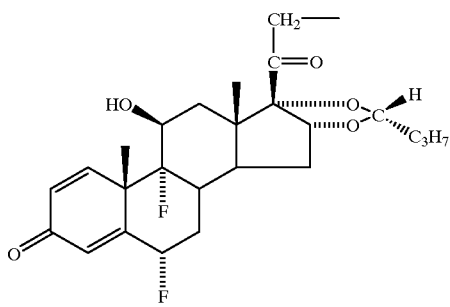

Sugar¹-OH can be chosen as a monosaccaride, a disaccaride or an oligosaccaride, e.g., D-glucose, D-glucuronic acid, D-galactose, D-galacturonic acid, D-cellobiose or D-lactose.

Preferably the Sugar¹ is β-linked D-glucose or D-glucuronic acid.

Most preferred compounds according to the invention are budesonide 22R-epimer β-D-glucoside, GCS¹ IV 22R-epimer β-D-glucoside and GCS¹ V 22R-epimer β-D-glucoside, budesonide 22R-epimer β-D-glucosiduronic acid, GCS¹ IV 22R-epimer β-D-glucosiduronic acid and GCS¹ V 22R-epimer β-D-glucosiduronic acid.

The compounds according to the present invention include an active GCS, which when released possesses high topical anti-inflamnmatory potency as well as undergoes profound hepatic first pass inactivation (85% or more). The combination of the GCS with a substantial first pass metabolism and a colon directed delivery provided by a bacteria specific enzymatic cleavage of the compound makes this possible.

Also comprised according to the present invention are pharmacologically and pharmaceutically acceptable salts of the compounds having the general formula GCS¹—O—Sugar¹.

METHODS OF PREPARATION

The compounds according to the invention are prepared by the condensation of a mono-, di- or oligosaccharide with a compound of the formulas VI, VI A, VI B and VII

VI

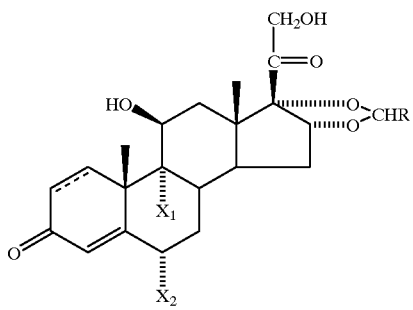

VIA

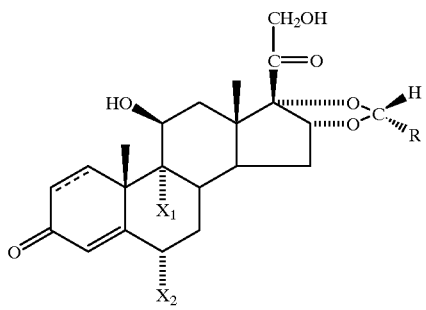

VIB

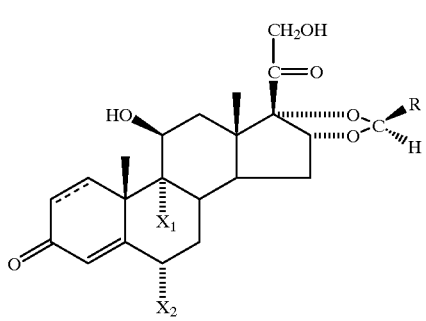

VII

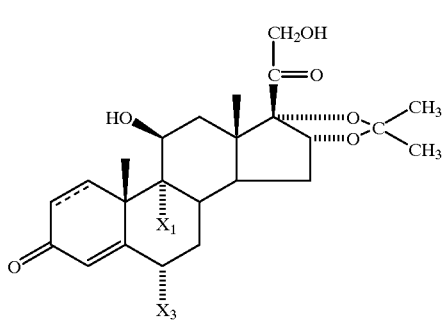

wherein the solid and broken lines between carbon 1 and carbon 2 represent a single or a double bond. R, $X_1$, $X_2$ and $X_3$ are as defined above.

The process according to the present invention to convert a compound of formulas VI, VI A, VI B and VII to the corresponding 21-glycosides is carried out by the condensation of a suitably protected derivative of the mono-, di- or oligosaccharide with the steroid or a derivative of the steroid, followed by deprotection of the condensation product.

Most suitable are glycosidation methods where the anomeric hydroxyl group of the glycosyl donor is exchanged for a better leaving group or a group which is transformed into a leaving group under the influence of a promoter. Preferably, glycosyl bromides and chlorides are condensed with alcohols with promoters such as silver trifluoromethanesulfonate, silver perchlorate, silver carbonate, mercury(II)bromide/mercury(II)cyanide, silver zeolite, zinc chloride or tetraethyl ammonium bromide. Glycosyl esters react with alcohols preferably under promotion of Lewis acids e.g. trimethylsilyl trifluoromethanesulfonate, tin (IV) chloride, tin(IV) chloride/silver perchlorate or boron trifluoride etherate. Alkyl and aryl thioglycosides can be reacted with alcohols using various thiophilic promoters, preferably N-iodosuccinimide/trifluoromethanesulfonic acid, iodonium dicollidine perchlorate, methylsulfenyl trifluoromethanesulfonate, methylsulfenyl bromide, benzeneselenyl trifluoromethanesulfonate, nitrosyl tetrafluoroborate, methyl trifluoromethanesulfonate, sulfuryl chloride/trifluoromethanesulfonic acid, dimethyl (methylthio)sulfonium trifluoromethanesulfonate or dimethyl(methylthio)sulfonium tetrafluoroborate. Glycosyl fluorides can use preferably trimethylsilyl trifluoromethanesulfonate, boron trifluoride etherate, tetrafluorosilane, titantetrafluoride, trifluoromethanesulfonic anhydride, tin(II)chloride/silver trifluoromethanesulfonate or tin II)chloride/silver perchlorate promotion. Glycosyl trichloroacetimidates can use Lewis acids such as trimethylsilyl trifluoromethanesulfonate or boron trifluoride etherate. n-Pentenyl glycosides can be activated with halonium ions preferably N-bromosuccinimide, iodonium dicollidine perchlorate or N-iodosuccinimide combined with trifluoromethanesulfonic acid, silver triflouromethanesulfonate or triethylsilyl trifluoromethanesulfonate. Furthermore 1,2-orthoesters, 1,2-oxazolines, 1,2-thioorthoesters, 1,2-cyanoethylidene derivatives, glycosyl thiocyanates, glycosyl sulfoxides, glycosyl sulfones, S-glycosyl xanthates, S-glycosyl dithiocarbamates, anhydrosugars and glycals can be used as glycosyl donors.

The pattern of protective groups of the glycosyl donor is of importance for the stereoselectivity of the glycosidic bond. Especially important is the protective group at the 2-position of the glycosyl donor. For example an acetyl or a benzoyl group at the 2-position of e.g. a glucosyl, glucosyluronate, galactosyl, galactosyluronate, cellobiosyl or lactosyl donor gives predominantly β-condensation. By using a so-called non-participating group e.g. allyl or benzyl at the 2-position of e.g. a galactosyl, galactosyluronate, glucosyl, glucosyluronate, cellobiosyl or lactosyl donor, these can be coupled mainly α to the steroid molecule. The solvent used for the condensation reaction is an aprotic solvent, preferably dichloromethane, chloroform, carbon tetrachloride, N,N-dimethylformamide, nitromethane, ethyl acetate, tetrahydrofuran, diethyl ether, toulene, dioxane, 1,2-dichloroethane, acetonitrile, monoglyme or a mixture of these. The solvent and the temperature often influence the stereochemical outcome of the reaction. For example, in the case of a galactosyl donor with a non-participating group at the 2-position e.g. diethyl ether often promotes α-condensation, whereas e.g. acetonitrile often promotes β-condensation.

In an alternative glycosidation method, the anomeric hydroxyl group of the glycosyl donor is reacted with a base e.g. sodium hydride and a derivative of the steroid where the 21-position has a suitable leaving group e.g. a trifluoromethanesulfonyl group. The glycosyl donor with an anomeric hydroxyl group can also be coupled to the steroid using various condensating reagents e.g. triphenylphosphine and diethyl azodicarboxylate. The mono-, di- or oligosaccharide can also be condensed with the steroid with a catalytic amount of e.g. trifluoromethanesulfonic acid in a suitable solvent e.g. dimethyl sulfoxide.

The protective groups of the condensation product can be removed by known methods. For example acyl protective groups are suitably removed by transesterification with e.g. sodium methoxide.

PHARMACEUTICAL PREPARATIONS

Further according to the invention conventional pharmaceutical preparations or pharmaceutical preparations that modestly retard the initial release of prodrug in cecum and colon ascendens, so that there will be a much more complete and continous exposition of active GCS over the most important colonic and sigmoidal regions are disclosed for the proper treatment of colonic inflammation.

This is accomplished by a pharmaceutical preparation containing the GCS prodrug protected with a coating that bursts after a pre-determined time, i.e. 5–10 hours after the preparation has left the stomach, when the preparation resides in the colon ascendens. The preparation is protected in the stomach by an enteric coating.

The objective is also accomplished by a pharmaceutical preparation containing the GCS prodrug protected by a polysaccharide that can be degraded by the gut microflora. The degree of protection should be adjusted so that the main part of release occurs after colon ascendens. The preparation could optionally be protected by an enteric coating.

The pharmaceutical preparations according to present invention are described more detailed in the following:

a) The GCS prodrug is formulated in a core through the well-known techniques granulation or granulation + extrusion + marumerization with suitable excipients including a super disintegrant e.g. crosslinked polyvinylpyrrolidone, sodium-CMC or sodium starch glycolate. The core is coated with a layer that will control the water penetration rate into the core. The layer can consist of an insoluble polymer e.g. ethylcellulose, hydroxypropylcellulose, Eudragit RS or Eudragit RL together with a hydrophobic agent e.g. a metal stearate. The proportions of the polymer and the metal stearate and/or the thickness of the layer will determine the lag time until the water has penetrated the layer and entered the core where the disintegrating agent will swell and rupture the membrane, releasing the GCS prodrug. The core and the layer is also coated with an enteric polymer e.g. Eudragit L, Eudragit S, cellulose acetate phtalate or hydroxypropylmethylcellulose phtalate which will prevent the water penetration when the formulation resides in the stomach.

b) The GCS prodrug is layered on a suitable core together with a suitable binding agent e.g. PVP or a water soluble cellulose ether in a fluid bed process or a rotor process. This core is coated with a layer containing a gut microflora degradable polysaccharide e.g. pectin, guar gum, dextran, carrageenan, amylose or chitosan in an insoluble polymer e.g. ethylcellulose, Eudragit R, Eudragit S or Eudragit NE. The time for degradation of the polysaccharide, so that the GCS prodrug can be released, can be altered by the proportion of the polysaccharide and insoluble polymer and/or the thickness of the layer. Optionally the layer can be protected by a layer of an enteric polymer e.g. Eudragit L, Eudragit S, cellulose acetate phtalate or hydroxypropylmethylcellulose phtalate.

WORKING EXAMPLES

The invention will be further illustrated by the following non-limitative examples. Concentrations were performed under reduced pressure at <40° C. bath temperature. Melting points were obtained with a Mettler FP82 Olympus BH-2 hot stage microscope. NMR spectra were recorded with a Varian VXR-300 instrument. The following reference signals were used:

Me$_4$Si, δ 0.00 ($^1$H in CDCl$_3$); and MeOH, δ 3.35 ($^1$H in CD$_3$OD). In the assignments below, atoms of glucose and glucuronic acid carry the superscript. Molecular weights were determined by fast atom bombardment (FAB) spectrometry. Column chromatography was performed on silica gel (60 Å, 40–63 μm; Merck, Darmstadt, Germany). HPLCanalyses were performed on a $C_{18}$ column (μBondapak 10 μmn 150×3.9 mm or Supelcosil 5 μm 150×4.6 mm) using acetonitrile/water or acetonitrile/20 mM TBAHS+10 mM phosphate buffer pH 7 as eluent. Powdered molecular sieves (4Å; Fluka, Buchs, Switzerland) were heated to 300° C. under vacuum overnight. Dichloromethane and toluene were dried over 4 Å molecular sieves, and methanol over 3 Å molecular sieves.

EXAMPLE 1

(22R) -16α, 17α-Butylidenedioxy-6α, 9α-difluoro-11β-hydroxy-4-pregnene-3,20-dione-21-yl β-D-glucopyranoside. (GCS[1] IV 22R-epimer β-D-glucoside).

A solution of silver trifluoromethanesulfonate (1.19 g, 4.64 mmol) in toluene (20 ml) was added during 5 minutes to a mixture of (22R)-16α, 17α-butylidenedioxy-6α, 9α-difluoro-11β,21-dihydroxy-4-pregnene-3,20-dione (1.09 g, 2.32 mmol), 2,3,4,6-tetra-o-benzoyl-α-D-glucopyranosyl bromide (2.30 g, 3.48 mmol) and powdered 4 Å molecular sieves (8.0 g) in dichloromethane (100 ml) at −20° C. under nitrogen. The temperature was allowed to rise to −10° C. during 1 h. Pyridine (3.0 ml) was added, and after additional 30 min stirring 0.5 M sodium thiosulfate (50 ml). The mixture was filtered through a layer of Celite. The organic phase was washed with water, 1 M sulfuric acid, water and saturated sodium hydrogen carbonate, dried over magnesium sulfate and concentrated. Chromatography (column: 50×4.0 cm, eluent: dichloromethane/ethyl acetate 9/1 by volume) gave amorphous (22R)-16α,17α-butylidenedioxy-6α,9α-difluoro-11β-hydroxy-4-pregnene-3,20-dione-21-yl 2',3',4',6'-tetra-o-benzoyl-β-D-glucopyranoside (2.03 g, 83%).

HPLC-analysis showed 96.4% purity.

$^1$H-NMR (CDCl$_3$): δ0.92 (t, H-25), 0.95 (s, H-18), 1.41 (m, H-24), 1.56 (s, H-19), 4.01 (m, H-5'), 4.39 (m, H-11), 4.55 (t, H-22), 4.89 (d, H-16), 5.25 (d, J$_{1,2}$=7.9 Hz, H-1'), 5.29 (2 m, H-6), 5.54 (dd, H-2$^1$), 5.75 (t, H-4'), 5.91 (t, H-3'), 6.15 (broad s, H-4).

MS showed an [M+Na]$^+$ ion of mlz 1069. (The calculated nuclide mass sum is 1046.4.)

Sodium methoxide in methanol (4.0 ml,0.5M) was added to a solution of this material (1.11 g, 1.06 mmol) in dichloromethane/methanol (50 ml, 1/3 by vol) at room temperature. After stirring overnight, the solution was neutralized with Dowex 50 (H$^+$) resin, filtered and concentrated. Chromatography (column: 30×4.0 cm, eluent:

dichloromethane/methanol 5/1 by vol) gave the title compound as an amorphous material (554 mg, 83%).

HPLC-analysis showed 97% purity.

$^1$H-NMR (CD$_3$OD): δ3 0.96 (s, H-18), 0.99 (t, H-25), 1.51 (m, H-24), 1.60 (s, H-19), 3.70 (m, H-6'a), 3.93 (broad d, H-6'b), 4.33 (m, H-11), 4.38 (d,J$_{1,2}$=7.6 Hz, H-1'), 4.60 (d, H-21a), 4.72 (t, H-22), 4.89 (d, H-21b), 5.45 (2m, H-6), 6.05 (broad s, H-4).

MS showed an [M+H]$^+$ion of m/z 631, and an [M+H]$^+$ion of m/z 653. (The calculated nuclide mass sum is 630.3).

EXAMPLE 2

(22R)-16α,17α-Butylidenedioxy-11β-hydroxypregna-1,4-diene-3,20-dione-21-yl β-D-glucopyranoside (Budesonide 22R-epimer β-D-glucoside).

Budesonide (1.00 g, 2.32 mmol) was reacted with 2,3,4, 6-tetra-o-benzoyl-α-D-glucopyranosyl bromide (2.30 g, 3.48 nmmol) analogously to that described in example 1. Chromatography (column: 50×4.0 cm, eluent:

dichloromethane/ethyl acetate 7/1 by vol) gave amorphous (22RS)-16α,17α-butylidenedioxy-11β-hydroxypregna-1,4-diene-3,20-dione-21-yl 2',3',4',6'-tetra-o-benzyol-5-β-D-glucopyranoside (1.96 g, 84%).

HPLC-analysis showed 98.8% purity.

$^1$H-NMR (CDCl$_3$): 0.87 (t, H-(S)25), 0.90 (t, H-(R)25), 0.98 (s, H-(R)18), 1.02 (s, H-(S)18), 1.50 (s, H-(RS)19), 5.21 (d, J$_{1,2}$=7.8 Hz, H-(S)1'), 5.23 (d, J$_{1,2}$=7.8 Hz, H-(R) 1'), 5.54 (dd, H-(R)2'), 5.56 (dd, H-(S)2'), 5.74 (t, H-(S)4'), 5.76 (t, H-(R)4'), 5.92 (t, H-(RS)3'), 6.03 (broad s, H-(RS)4), 6.29 (dd, H-(S)2), 6.31 (dd, H-(R)2).

MS showed an [M+Na]$^+$ion of m/z 1031. (The calculated nuclide mass sum is 1008.4) This material (1.22 g, 1.21 mmol) was deacylated and purified analogously to that described in example 1. The 22R- and 22S-epimers of the obtained material (674 mg, 94%) were separated by semi-preparative HPLC (Apex Prepsil ODS 8 μm, 25x2.25 cm) using acetonitrile/water 23/77 as eluent. This gave the title compound as an amorphous material (280 mg, 83%).

HPLC-analysis showed 98.5% purity.

$^1$H-NMR(CD$_3$OD): δ0.96 (t, H-25), 0.99 (s, H-18), 1.46 (m, H-24), 1.53 (s, H-19), 3.69 (m, H-6'a), 3.93 (d, H-6'b), 4.37 (d, J$_{1,2}$,7.7 Hz, H-1'), 4.47 (m, H-11), 4.59 (d, H-21a), 4.67 (t, H-22), 4.86 (d, H-21b), 4.90 (d, H-16), 6.06 (broad s, H-4), 6.30 (dd, H-2), 7.50 (d, H-1). MS showed an [M+Na]$^+$ion of m/z 615, and an [M+H]$^+$ion of m/z 593. (The calculated nuclide mass sum is 592.3).

EXAMPLE 3

Sodium [(22R)-16α,17α-butylidenedioxy-6α,9α-difluoro-11β-hydroxy-4-pregnene-3,20-dione-21-yl β-D-glucopyranosid]uronate (GCS[1]IV 22R-epimer β-D-glucosiduronate).

A solution of silver trifluoromethanesulfonate (1.38 g, 5.38 mmol) in toluene (25 ml) was added during 15 min to a mixture of (22R)-16α,17α-butylidenedioxy-6α,9α-difluoro-11β-dihydroxy-4-pregnene-3,20-dione (1.20 g, 2.56 mmol), methyl (2,3,4-tri-o-benzoyl-α-D-glucopyranosyl bromide)uronate (2.39 g, 4.10 mmol) and powdered 4A molecular sieves (9.0 g) in dichloromethane/toluene (125 ml, 4/1 by vol) at −20° C. under nitrogen. The temperature was allowed to rise to 10° C. during 2 h. Pyridine (5.0 ml) was added, followed by 0.5 M sodium thiosulfate (70 ml). The reaction mixture was worked up as described in example 1. Chromatography (column: 50×4.0 cm, eluent: toluene/dichloromethane/ethyl acetate 40/20/15 by vol) gave amorphous methyl [(22R)-16α, 17α-butylidenedioxy-6α, 9α-difluoro-11β-hydroxy-4-pregnene-3,20-dione-21-yl 2',3', 4'-tri-o-benzoyl-β-D-glucopyranosid]uronate (1.59 g, 64%).

HPCL-analysis showed 97.7% purity.

$^1$H-NMR(CDCl$_3$): δ0.89 (s, H-18), 0.94 (t, H-25), 1.44 (m, H-24), 1.53 (s, H-19), 3.64 (s, COOCH$_3$), 4.34 (d, H-5'), 4.44 (m, H-11), 4.54 (d, H-21a), 4.60 (t, H-22), 4.90 (d, H-16), 4.91 (d, H-21b), 5.25 (d, J$_{1,2}$=7.6 Hz, H-1'), 5.28 (2 m, H-6), 5.58 (dd, H-2'), 5.67 (t, H-4'), 5.94 (t, H-3'), 6.15 (broad s, H-4).

MS showed an [M+Na]$^+$ion of m/z 993. (The calculated mass sum is 970.4.)

Litium hydroxide in water (9.1 ml, 1.0 M) was added to a solution of this material (1.38 g, 1.42 mmol) in tetrahydrofuran/water (65 ml, 3/1 by vol) at 0° C. The solution was allowed to attain room temperature, and after stirring for 24 h the solution was neutralized with acetic acid (1.0 ml) and concentrated. The residue was purified by semipreparative HPLC (Apex Prepsil ODS 8 μm, 25×2.25 cm) using ethanol/40 mM aqueous triethylammonium acetace pH 5.0 33/67 as eluent. Fractions containing the desired substance were pooled, desalted on a C-18 column (10 g, Isolute; International Sorbent Technology, Hengoed, Mid Glamorgan, U.K.) using a stepwise water/methanol gradient, and converted into the sodium form by ion exchange on a column (4×2.5 cm) of Dowex 50Wx2 ($Na^+$-form). Lyophilization gave the title compound as an amorphous material (305 mg, 32%).

HPLC-analysis showed 97.3% purity.

$^1$H-NMR($CD_3OD$): δ0.95 (s, H-18), 0.99 (t, H-25), 1.51 (m, H-24), 1.60 (s, H-19), 4.35 (m, H-11), 4.44 (d, $J_{1,2}$,=7.6 Hz, H-1'), 4.73 (t, H-22), 4.74 (d, H-21a), 5.45 (2m, H-6), 6.05 (broad s, H-4).

EXAMPLE 4

Sodium [(22R)-16α, 17α-butylidenedioxy-11β-hydroxypregna-1,4-diene-3,20-dione-21-yl β-D-glucopyranosid]uronate (Budesonide 22R-epimer β-D-glucosiduronate).

A solution of silver trifluoromethanesulfonate (238 mg, 0.928 mmol) in toluene (4.0 ml) was added to a mixture of (22R)-16α,17α-butylidenedioxy-11β,21-dihydroxypregna-1,4-diene-3,20-dione (200 mg, 0.464 mmol), methyl (2,3,4-tri-o-benzoyl-α-D-glucopyranosyl bromide)uronate (406 mg, 0.696 mmol) and powdered 4A molecular sieves (1.2 g) in dichloromethane (10 ml) at −50° C. under nitrogen. The temperature was allowed to rise to 0° C. during 2 h. Pyridine (600 gl) was added, followed by 0.5 M sodium thiosulfate (10 ml). The reaction mixture was worked up as described in example 1. Chromatography (column: 30×3.0 cm, eluent: dichloromethane/ethyl acetate 5/1 by vol) gave amorphous methyl [(22R)-16α,17(-butylidenedioxy-11β-hydroxypregna-1,4-diene-3,20-dione-21-yl 2',3',4'-tri-o-benzoyl-β-D-glucopyranosid]uronate (397 mg, 91%).

HPCL-analysis showed 99.0% purity.

$^1$H-NMR($CDCl_3$): 5 0.92 (s, H-18), 0.92 (t, H-25), 1.40 (m, H-24), 3.67 (s, $COOCH_3$), 4.33 (d, H-5'), 4.54 (m, H-11,21a,22), 4.87 (d, H-16), 4.87 (d, H-21b), 5.25 (d,$J_{1,2}$,=7.3 Hz, H-1'), 5.57 (dd, H-2'), 5.70 (t, H-4'), 5.93 (t, H-3'), 6.03 (broad s, H-4) 6.30 (dd, H-2).

MS showed an [M+Na]+ion of m/z 955. (The calculated nuclide mass sum is 932.4).

Litium hydroxide in water (2.5 ml, 1.0 M) was added to a solution of this material (360 mg, 0.386 mmol) in tetrahydrofuran/water (18 ml, 3/1 by vol) at 0° C. The solution was allowed to attain room temperature, and after 22 h the solution was neutralized with acetic acid (290 μl) and concentrated. Chromatography (column: 30×2.0 cm, eluent: ethyl acetate/acetic acid/methanol/water 16/3/3/2 by vol), followed by desalting, ion exchange and lyophilization as described in example 3 gave the title compound as an amorphous material (220 mg, 91%).

HPLC-analysis showed 98.2% purity.

$^1$H-NMR($CD_3OD$): δ0.96 (s, H-25), 0.98 (s, H-18), 1.47 (m, H-24), 1.53 (s, H-19), 4.43 (d, $J_{1,2}$, 7.6 Hz, H-1') 4.48 (m, H-11), 4.68 (t, H-22), 4.71 (d, H-21a), 4.86 (d, H-21b), 4.89 (d, H-16), 6.05 (broad s, H-4), 6.30 (dd, H-2), 7.52 (d, H-1).

The following non-limitative examples illustrate pharmaceutical preparations suitable for the compounds of the invention.

EXAMPLE 5

Tablet

Tablets are prepared by conventional compression methods with the following composition

| | |
|---|---|
| Budesonide 22R-epimer β-D-glucoside, budesonide 22R-epimer β-D-glucosiduronate, $GCS^1$ IV 22R-epimer β-D-glucoside or $GCS^1$ IV 22R-epimer β-D-glucosiduronate | 5 mg |
| Lactose | 80 mg |
| Microcrystalline cellulose | 20 mg |
| Crosspovidone | 5 mg |
| Polyvinylpyrrolidone | 5 mg |
| Magnesium stearate | 2 mg |

EXAMPLE 6

Enteric tablet

| | |
|---|---|
| Eudragit L30D | 3.7 mg |
| PEG 6000 | 0.4 mg |
| Talc | 0.9 mg |

EXAMPLE 7

Delayed release capsule

Budesonide 22R-epimer β-D-glucoside, budosenide 22R-epimer β-D-glucosiduronate, $GCS^1$ IV 22R-epimer β-D-glucoside or $GCS^1$IV 22R-epimer β-D-glucosiduronate (7.1 g) is mixed with 300 g lactose, 128 g microcrystalline cellulose, 75 g crosslinked polyvinylpyrrolidone and 25 g polyvinylpyrrolidone. The mixture is granulated with water and the wet mass is extruded and spheronized giving cores with approximative size of 1 mm. The cores are dried and sieved. The cores are coated with a mixture of 255 g Eudragit NE30D, 77 g magnesium stearate and 250 g water in a fluid bed apparatus. Finally an enteric coating consisting of 11 g Eudragit L30D dispersion, 3 g triethylcitrate and 15 g talc is sprayed on the spheres. The pellets are dried in the fluid bed apparatus, sieved and filled in hard gelatine capsules.

EXAMPLE 8

Gut microflora controlled release capsule

Budesonide 22R-epimer β-D-glucoside or budesonide 22R-epimer β-D-glucosiduronate (6.6 g) is suspended in a solution of 1 g of hydroxypropylmethylcellulose in 50 ml of water. The mixture is sprayed on to 510 g sugar spheres in a fluid bed apparatus. Thereafter a mixture of 85 g guar gum, 30 g (solid content) Eudragit RL30D and 15 g talc in totally 900 g of a 1:1 mixture of water and isopropanol is sprayed on the spheres. Finally an enteric coating consisting of 100 g Eudragit L30D dispersion, 3 g triethylcitrate and 15 g talc is sprayed on the spheres. The pellets are dried in the fluid bed apparatus, sieved and filled into hard gelatine capsules.

EXAMPLE 9

Gut microflora controlled release capsule $GCS^1$ IV 22R-epimer β-D-glucoside or $GCS^1$IV 22R-epimer β-D-glucosiduronate (6.8 g) is suspended in a mixture of 15 g locust bean gum, 5 g (solid content) Eudragit RL30D and 2 g talc in totally 220 g of a 1:1 mixture of water and isopropanol. This mixture is sprayed on to 510 g of sugar spheres in a fluid bed apparatus. Then a mixture of 80 g locust bean gum, 40 g (solid content) Eudragit RL30D and 15 g talc in totally 900 g of a 1:1 mixture of water and isopropanol is sprayed on the spheres. Finally an enteric coating consisting of 100 g Eudragit L30D dispersion, 3 g triethylcitrate and 15 g talc is sprayed on the spheres.

The pellets are dried in the fluid bed apparatus, sieved and filled in hard gelatine capsules.

Pharmacological testing

The anticolitic activity of the new prodrugs has been demonstrated in the colitis model described below. To judge that the prodrugs fulfil the intended profile and are broken down in the gut to active glucocorticosteroids, the model has been designed so that the compounds have been administered orally and the anti-inflammatory activity judged in distal colon.

In vivo test model

Oxazolone-induced colitis in rats. This is an IBD-model in rats, creating a T-cell dependent colitis after intra-rectal challenge of the hapten oxazolone in previously skin-sensibilized animals. The inflammation starts with an acute stage that 24 hours after challenge shows infiltration of inflammatory cells, an increased colon-wet weight (edema), hyperaemia and slight ulcerations. After some days more chronic inflammation has developed with a persistent wet-weight increase and with a dominance of T-cells in the cell-infiltrate.

Experimental procedures

Dark Agouti rats were sensitized by painting 12 mg oxazolone (in 0.3 ml acetone/95% ethanol (1:4) on the skin on two consecutive days. Seven days after the second sensitization, the animals were challenged in the colon via a rectal injection of 6 mg oxazolone emulsified in 200 µl of equal parts Orabase® and peanut-oil. After sacrificing the animals four days after challenge, the distal colon was weighed to obtain the wet-weight. The colitis was measured as edema (increase of wet-weight of distal colon over that of saline treated normals). Thymus weight was recorded as an unwanted systemic glucocorticoid activity.

Treatment

The glucocorticosteroid-glycosides were dissolved in a minute amount of ethanol and diluted with 0.9% NaCl. The animals received 30 or 300 nmol/kg bodyweight of the steroids orally (by gavage 10 ml/kg body weight) for three days, starting the day after challenge. Control animals were treated with NaCl. The treatment groups included 6 animals.

Results

| GCS and dose (nmol/kg) | Colon edema (% of colitic controls) | Thymus weight (% of colitic controls) |
|---|---|---|
| Budesonide 30 | 101 ± 15 | 96 ± 4 |
| Budesonide 300 | 85 ± 19 | 54 ± 3 |
| Budesonide β-D-glucosiduronate 30 | 90 ± 17 | 77 ± 7 |
| Budesonide β-D-glucosiduronate 300 | 58 ± 4 | 45 ± 6 |
| GCS$^1$ IV 22-R-epimer β-D-glucosiduronate 30 | 73 ± 12 | 86 ± 4 |
| GCS$^1$ IV 22-R-epimer β-D-glucosiduronate 300 | 37 ± 8 | 36 ± 2 |
| GCS$^1$ V 22-R-epimer β-D-glucosiduronate 30 | 28 ± 6 | 84 ± 4 |
| GCC$^1$ V 22-R-epimer β-D-glucosiduronate 300 | 0 ± 9 | 32 ± 3 |

Conclusion:

The table shows that GCS$^1$ IV 22-R-epimer β-D-glucosidoronate and GCS$^1$ V 22 -R-epimer β-D-glucosiduronate have a higher oral anticolitic potency and efficacy than GCS$^1$ IV 22-R-epimer β-D-glucosiduronate and GCS$^1$ V 22-R-epimer β-D-glucosiduronate, budesonide and budesonide β-D-glucosiduronate. While the latter compounds at the dose 300 nmol/kg reduced the colonic edema by maximally about 40%, the two new compounds at the same dose inhibited the edema by about 65% or even fully blunted the edema. GCS$^1$ V 22-R-epimer β-D-glucosiduronate induced a much stronger inhibition at the dose 30 nmol/kg than did budesonide or budesonide β-D-glucosiduronate at 300 nmol/kg, showing that GCS$^1$ V 22R-epimer β-D-glucosiduronate was more than 10 times as potent as busesonide or buesonide β-D-glucosiduronate. GCS$^1$ IV 22-R-epimer β-D-glucosiduronate and GCS$^1$ V 22-R-epimer β-D-glucosiduronate also achieved a markedly better relation between antiedema efficacy and thymus involution, which involution represents an unwanted systemic glucocorticoid activity. This is obvious when the three β-D-glucosiduronates are compared at the same dose levels: while the extent of thymus involution does not differ so much, the colonic antiedema efficacy is much stronger for GCS$^1$ IV 22 R-epimer β-D-glucosiduronate and GCS$^1$ V 22R-epimer β-D-glucosiduronate.

What is claimed is:

1. A method for local treatment of inflamed bowel mucosa in mammals, whereby an effective amount of a compound of the general formula GCS$^1$-O-Sugar$^1$ is administered to a host in need of such treatment, wherein GCS$^1$ is a moiety selected from the group consisting of (a) an epimeric mixture of a moiety according to formula I,

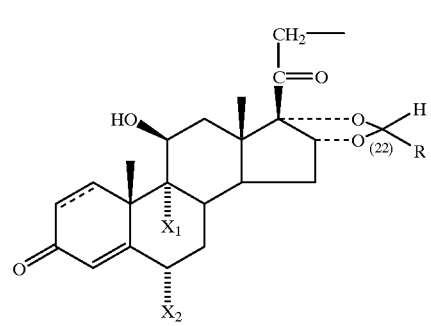

(b) the corresponding pure 22R-epimer, (c) the corresponding pure 22S-epimer, and (d) a moiety according to formula II

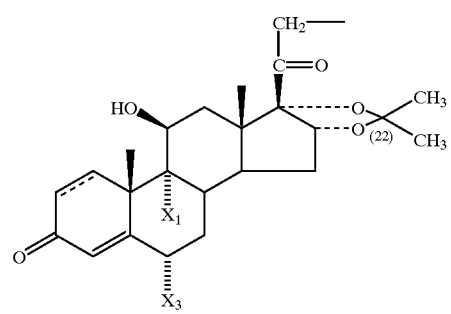

wherein $X_1$ and $X_2$ are independently selected from the group consisting of hydrogen, fluoro, chloro and bromo substituents; $X_3$ is selected from the group consisting of fluoro, chloro and bromo substituents; R is a hydrocarbon chain with 1–9 carbon atoms; the 1,2-position in each of said formulas is a saturated bond or double bond; and -0-Sugar$^1$ deonotes a sugar selected from the group consisting of a monosaccharide, a disaccharide, and an oligosaccharide, linked to the C-21 methylene group of GCS$^1$ via a glycosidic bond, as well as a pharmaceutically acceptable salt thereof, wherein the compound GCS$^1$-OH is a glucocorticosteroid with a high hepatic first pass metabolism.

2. A method for the local treatment of the bowel segments mostly affected by inflamed bowel disease in mammals, whereby an effective amount of a compound of the general formula GCS$^1$-O-Sugar$^1$ is administered to a host in need of such treatment, wherein GCS$^1$ is a moiety selected from the group consisting of (a) an epimeric mixture of a moiety according to formula I,

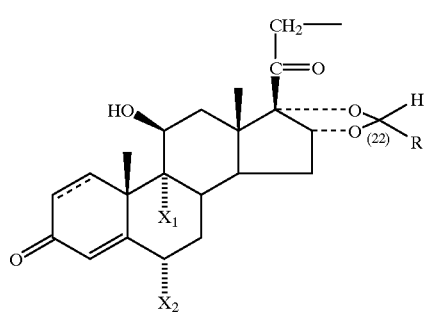

I (b) the corresponding pure 22R-epimer, (c) the corresponding pure 22S-epimer, and (d) a moiety according to formula II

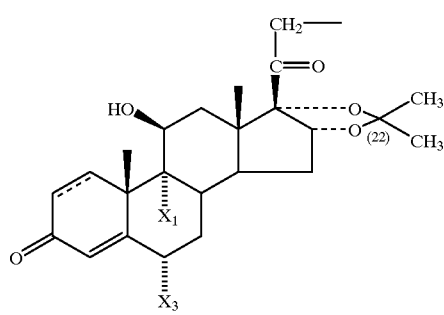

II wherein $X_1$ and $X_2$ are independently selected from the group consisting of hydrogen, fluoro, chloro and bromo substituents; $X_3$ is selected from the group consisting of fluoro, chloro and bromo substituents; R is a hydrocarbon chain with 1–9 carbon atoms; the 1,2-position in each of said formulas is a saturated bond or double bond; and —O-Sugar$^1$ denotes a sugar selected from the group consisting of a monosaccharide, a disaccharide, and an oligosaccharide, linked to the C-21 methylene group of GCS$^1$ via a glycosidic bond, as well as a pharmaceutically acceptable salt thereof, wherein the compound GCS$^1$ —OH is a glucocorticosteroid with a high hepatic first pass metabolism.

3. A method for the local treatment of colitis, comprising administration of an effective amount of a compound of the general formula GCS$^1$-O-Sugar$^1$ to a patient in need of such treatment, wherein GCS$^1$ is a moiety selected from the group consisting of (a) an epimeric mixture of a moiety according to formula I,

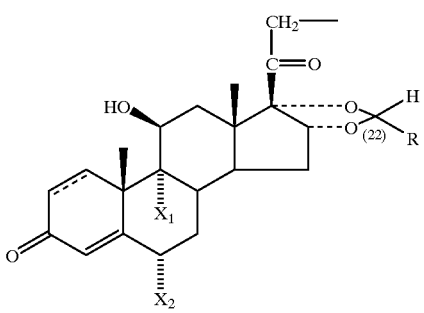

I (b) the corresponding pure 22R-epimer, (c) the corresponding pure 22S-epimer, and (d) a moiety according to formula II,

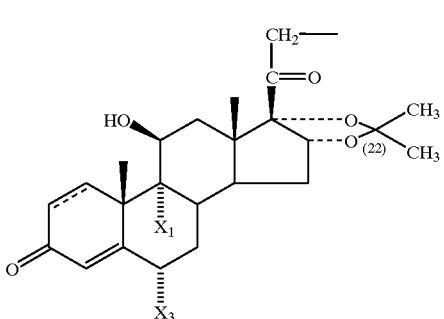

II wherein $X_1$ and $X_2$ are independently selected from the group consisting of hydrogen, fluoro, chloro and bromo substituents; $X_3$ is selected from the group consisting of fluoro, chloro and bromo substituents; R is a hydrocarbon chain with 1–9 carbon atoms; the 1,2-position in each of said formulas is a saturated bond or double bond; and —O-Sugar$^1$ denotes a sugar selected from the group consisting of a monosaccharide, a disaccharide, and an oligosaccharide, linked to the C-21 methylene group of GCS$^1$ via a glycosidic bond, as well as a pharmaceutically acceptable salt thereof, wherein the compound GCS$^1$—OH is a glucocorticosteroid with a high hepatic first pass metabolism, provided that the compound GCS$^1$-O-Sugar$^1$ is incorporated into a formulation which optimally releases the GCS$^1$ over the middle and distal parts of the patient's colon.

4. A method for the local treatment of small bowel inflammation associated with Morbus Crohn in mammals, including man, whereby an effective amount of a compound of the general formula GCS$^1$ -O-Sugar$^1$ is administered to a host in need of such treatment, wherein GCS$^1$ is a moiety selected from the group consisting of (a) an epimeric mixture of a moiety according to formula I,

I

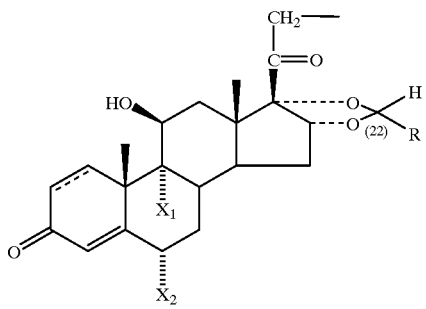

22R-epimer, and (d) a moiety according to formula II,

II

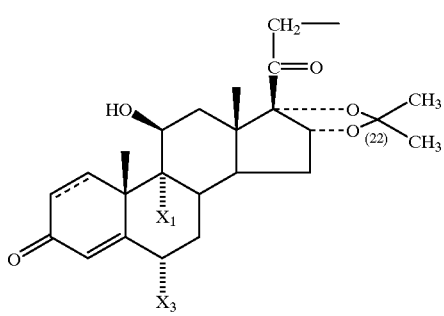

wherein $X_1$ and $X_2$ are independently selected from the group consisting of hydrogen, fluoro, chloro and bromo substituents; $X_3$ is selected from the group consisting of fluoro, chloro and bromo substituents; R is a hydrocarbon chain with 1–9 carbon atoms; the 1,2-position in each of said formulas is a saturated bond or double bond; and —O-Sugar[1] denotes a sugar selected from the group consisting of a monosaccharide, a disaccharide, and an oligosaccharide, linked to the C-21 methylene group of GCS[1] via a glycosidic bond, as well as a pharmaceutically acceptable salt thereof, wherein the compound GCS[1]—OH is a glucocorticosteroid with a high hepatic first pass metabolism.

5. The method of claim 1, wherein the GCS[1] is the 22R-epimer of formula I.

6. The method of claim 1, wherein the GCS[1] is selected from the group consisting of the 22R-epimer of the budesonide moiety of formula III,

III

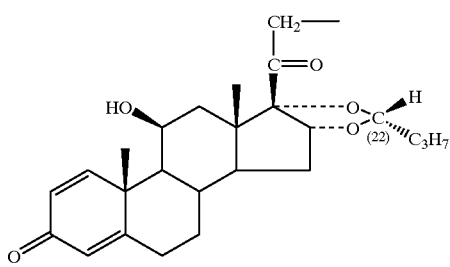

and the 22R-epimer of formula IV,

IV

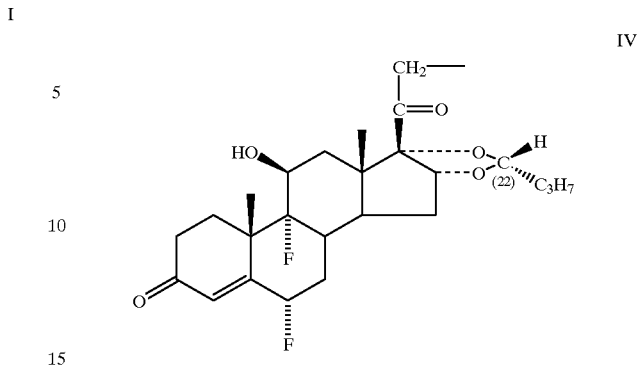

and the 22R-epimer of formual V,

V

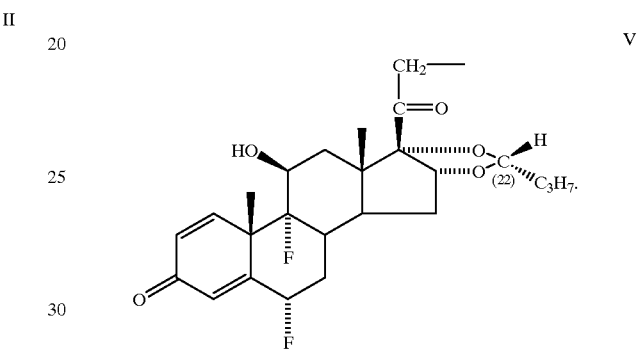

7. The method of claim 1, wherein the Sugar[1]-OH is selected from the group consisting of D-glucose, D-galactose, D-cellobiose and D-lactose.

8. The method of claim 5, wherein the Sugar[1] -OH is selected from the group consisting of D-glucose, D-galactose, D-cellobiose and D-lactose.

9. The method of claim 6, wherein the Sugar[1]—OH is selected from the group consisting of D-glucose, D-galactose, D-cellobiose and D-lactose.

10. The method of claim 1, wherein the Sugar[1]-OH is β-linked D-glucose.

11. The method of claim 5, wherein the GCS[1] -O-Sugar[1] is (22R)-16α,17α-butylidenedioxy-6α-9α-difluoro-11μhydroxy-4-pregnene-3,20 dione-21-yl β-D-glucopyranoside.

12. The method of claim 5, wherein the GCS[1] -O-Sugar[1] is (22R)-16α,17α-butylidenedioxy-11βg-hydroxypregna-1,4-diene-3,20 dione-21-yl β-D-glucopyranoside.

13. The method of claim 2, wherein the GCS[1]-O-Sugar[1] is sodium [(22R)-16α,17α-butylidenedioxy-6α,9α-difluoro-11β-hydroxypregna-1,4-diene-3,20-dione-21-yl-β-D-glucopyranosid]uronate.

14. The method of claim 2, wherein the GCS[1] is the 22R-epimer of formula I.

15. The method of claim 2, wherein the GCS[1] is selected from the group consisting of the 22R-epimer of the budesonide moiety of formula III,

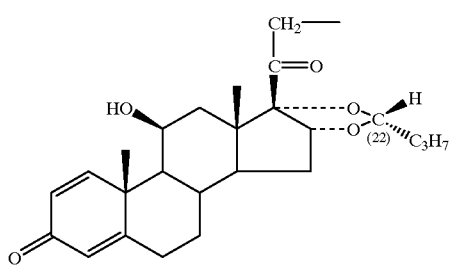

III and the 22R-epimer of formula IV,

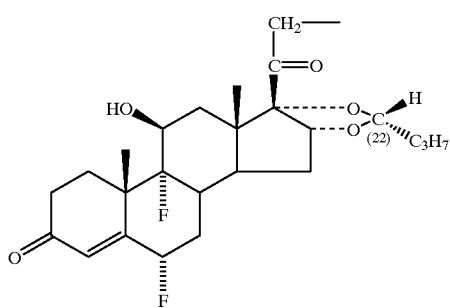

IV and the 22R-epimer of formula V,

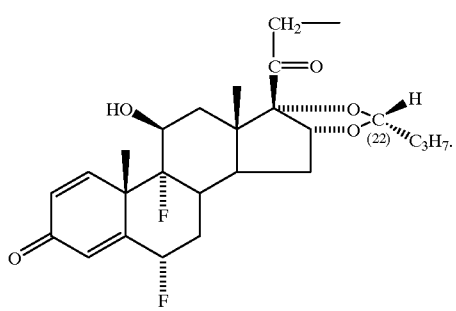

III

16. The method of claim 2, wherein the Sugar[1]-OH is selected from the group consisting of D-glucose, D-galactose, D-cellobiose and D-lactose.

17. The method of claim 14, wherein the Sugar[1]-OH is selected from the group consisting of D-glucose, D-galactose, D-cellobiose and D-lactose.

18. The method of claim 15, wherein the Sugar[1]-OH is selected from the group consisting of D-glucose, D-galactose, D-cellobiose and D-lactose.

19. The method of claim 2, wherein the Sugar[1]-OH is β-linked D-glucose.

20. The method of claim 14, wherein the GCS[1]-O-Sugar[1] is (22R)-16α,17α-butylidenedioxy-6α,9α-difluoro-11α-hydroxy-4-pregnene-3,20 dione-21-yl-6 2-D-glucopyranoside.

21. The method of claim 3, wherein the GCS[1]-O-Sugar[1] is (22R)-16α,17α-butylidenedioxy-11β-hydroxypregna-1,4-diene-3,20 dione-21-yl β-D-glucopyranoside.

22. The method of claim 2, wherein the GCS[1]-O-Sugar[1] is sodium [(22R)-16α,17α-butylidenedioxy-6α,9α-difluoro-11β-hydroxypregna-1,4-diene-3,20-dione-21-yl-β-D-glucopyranosid]uronate.

23. The method of claim 3, wherein the GCS[1] is the 22R-epimer of formula I.

24. The method of claim 3, wherein the GCS[1] is selected from the group consisting of the 22R-epimer of the budesonide moiety of formula III,

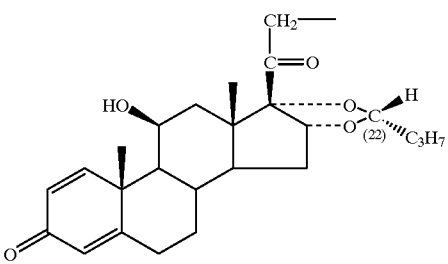

III and the 22R-epimer of formula IV,

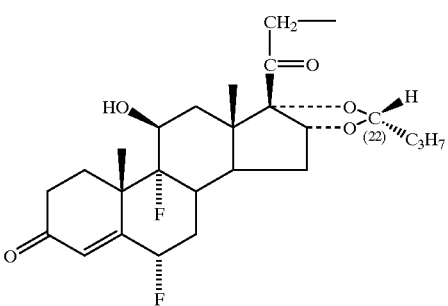

IV and the 22R-epimer of formula V,

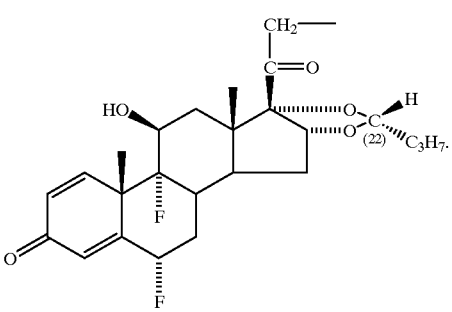

V

25. The method of claim 3, wherein the Sugar[1]-OH is selected from the group consisting of D-glucose, D-galactose, D-cellobiose and D-lactose.

26. The method of claim 23, wherein the Sugar[1]-OH is selected from the group consisting of D-glucose, D-galactose, D-cellobiose and D-lactose.

27. The method of claim 24, wherein the Sugar[1]-OH is selected from the group consisting of D-glucose, D-galactose, D-cellobiose and D-lactose.

28. The method of claim 3, wherein the Sugar[1]-OH is linked D-glucose.

29. The method of claim 23, wherein the GCS[1]-O-Sugar[1] is (22R)-16α,17α-butylidenedioxy-6α, 9α-difluoro-11β-hydroxy-4-pregnene-3,20 dione-21-yl β-D-glucopyranoside.

30. The method of claim 23, wherein the GCS[1]-O-Sugar[1] is (22R)-16α,17α-butylidenedioxy-11β-hydroxypregna-1,4-diene-3,20 dione-21-yl β-D-glucopyranoside.

31. The method of claim 3, wherein the GCS$^1$-O-Sugar$^1$ is sodium [(22R)-16α,17α-butylidenedioxy-6α,9α-difluoro-11β-hydroxypregna-1,4-diene-3,20-dione-21-yl-β-D-glucopyranosid]uronate.

32. The method of claim 4, wherein the GCS$^1$ is the 22R-epimer of formula I.

33. The method of claim 4, wherein the GCS$^1$ is selected from the group consisting of the 22R-epimer of the budesonide moiety of formula III,

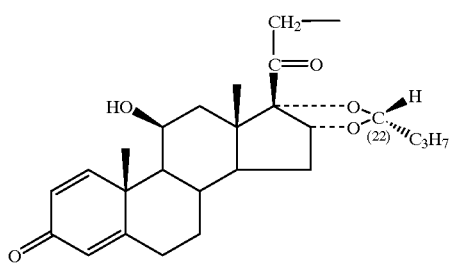

III and the 22R-epimer of formula IV,

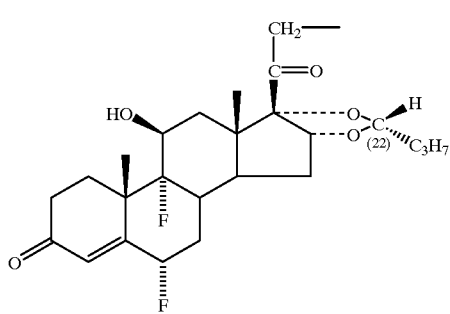

IV and the 22R-epimer of formula V,

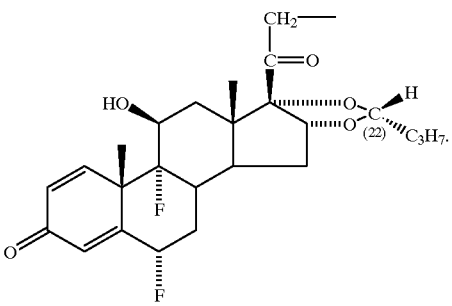

V

34. The method of claim 4, wherein the Sugar$^1$-OH is selected from the group consisting of D-glucose, D-galactose, D-cellobiose and D-lactose.

35. The method of claim 32, wherein the Sugar$^1$-OH is selected from the group consisting of D-glucose, D-galactose, D-cellobiose and D-lactose.

36. The method of claim 33, wherein the Sugar$^1$-OH is selected from the group consisting of D-glucose, D-galactose, D-cellobiose and D-lactose.

37. The method of claim 4, wherein the Sugar$^1$-OH is β-linked D-glucose.

38. The method of claim 32, wherein the GCS$^1$-O-Sugar$^1$ is (22R)-16α, 17α-butylidenedioxy-6α-9α-difluoro-11β-hydroxy-4-pregnene-3,20 dione-21-yl β-D-glucopyranoside.

39. The method of claim 4, wherein the GCS$^1$-O-Sugar$^1$ is (22R)-16α,17α-butylidenedioxy-11β-hydroxypregna-1,4-diene-3,20 dione-21-yl β-D-glucopyranoside.

40. The method of claim 1, wherein the host is a human.

41. The method of claim 2, wherein the host is a human.

42. The method of claim 3, wherein the patient is a human.

43. The method of claim 4, wherein the host is a human.

* * * * *

UNITED STATES PATENT AND TRADEMARK OFFICE
CERTIFICATE OF CORRECTION

PATENT NO.    : 6,140,308
DATED         : October 31, 2000
INVENTOR(S)   : Ralph Brattsand et al.

It is certified that error appears in the above-identified patent and that said Letters Patent is hereby corrected as shown below:

Column 3,
Line 42, delete "selected for the group" and insert -- selected from the group --
Line 47, delete "GSC$^1$ a saturated" and insert -- GCS$^1$ is a saturated --.
Line 48, delete "bond.6" and insert -- bond. --.
Lines 54-65, delete duplicate diagram.

Column 7,
Line 11, delete "or tin II)" and insert -- or tin(II) --.

Column 8,
Line 64, delete "the superscript" and insert -- the ' superscript --.

Column 9,
Line 2, delete "$\mu$mn" and insert -- $\mu$m --.
Lines 18, 31 and 65, delete "tetra-o-benzoyl" and insert -- tetra-O-benzoyl --.
Line 40, delete "ion of mlz" and insert -- ion of m/z --.

Column 10,
Lines 4, 40 and 51, delete "tetra-o-benzoyl" and insert -- tetra-O-benzoyl --.
Line 42, delete "powdered 4A" and insert -- powdered 4Å --.
Line 53, delete "HPCL" and insert -- HPLC --.
Line 63, delete "Litium" and insert -- Lithium --.

Column 11,
Line 22, delete "tetra-o-benzoyl" and insert -- tetra-O-benzoyl --.
Line 29, delete "powered 4A" and insert -- powdered 4Å --.
Line 32, delete "(600 gl)" and insert -- (600 $\mu$l) --.
Line 36, delete ",17( " and insert -- ,17$\alpha$ --.
Line 49, delete "Litium" and insert -- Lithium --.

Column 12,
Line 21, insert -- The tablet from Example 5 is coated with --.
Line 48, delete "microf lora" and insert -- microflora --.

Column 13,
Line 61, delete "GCC$^1$" and insert -- GCS$^1$ --.
Line 67, delete "glucosidoronate" and insert -- glucosiduronate --.

UNITED STATES PATENT AND TRADEMARK OFFICE
CERTIFICATE OF CORRECTION

PATENT NO.   : 6,140,308
DATED        : October 31, 2000
INVENTOR(S)  : Ralph Brattsand et al.

It is certified that error appears in the above-identified patent and that said Letters Patent is hereby corrected as shown below:

Column 14,
Lines 2-3, delete "GCS′ IV 22-R-epimer $\beta$-D-glucosiduronate and GCS′ V 22-R-epimer $\beta$-D-glucosiduronate".
Line 6, delete "the two new compounds" and insert -- GCS' IV 22-R-epimer $\beta$-D-glucosiduronate and GCS′ V 22-R-epimer $\beta$-D-glucosiduronate --.
Line 13, delete "busesonside or buesonide" and insert -- budesonide or budesonide --.

Column 16,
Line 62, delete "with Morbus Crohn" and insert -- Crohn's disease --.
Line 63, delete "including man, whereby" and insert -- whereby --.

Column 17,
Line 16, delete "22-R-epimer," and insert -- (b) The corresponding pure 22R-epimer, (c) the corresponding pure 22S-epimer, --

Column 18,
Line 51, delete "11 $\mu$ hydroxy-4-" and insert -- 11$\beta$hydroxy-4- --.
Line 55, delete "11$\beta$g-" and insert -- 11$\beta$ --.
Line 58, delete "of claim 2" and insert -- of claim 1 --.

Column 19,
Line 19, delete "III" and insert -- V --.
Line 58, delete "11$\alpha$" and insert -- 11$\beta$ --.
Line 59, delete "-62" and insert -- $\beta$ --.
Line 61, delete "of claim 3" and insert -- of claim 14 --.

UNITED STATES PATENT AND TRADEMARK OFFICE
CERTIFICATE OF CORRECTION

PATENT NO. : 6,140,308
DATED : October 31, 2000
INVENTOR(S) : Ralph Brattsand et al.

It is certified that error appears in the above-identified patent and that said Letters Patent is hereby corrected as shown below:

Column 20,
Line 60, delete "linked D-glucose" and insert -- $\beta$-linked D-glucose --.

Signed and Sealed this

Thirty-first Day of August, 2004

JON W. DUDAS
*Director of the United States Patent and Trademark Office*